United States Patent [19]

El-Bayoumy et al.

[11] Patent Number: 4,988,517

[45] Date of Patent: Jan. 29, 1991

[54] METHOD AND COMPOSITION FOR INHIBITING COLON CARCINOGENESIS

[75] Inventors: Karam El-Bayoumy, New Rochelle; Bandaru S. Reddy, Suffern, both of N.Y.

[73] Assignee: American Health Foundation, Valhalla, N.Y.

[21] Appl. No.: 249,845

[22] Filed: Sep. 27, 1988

[51] Int. Cl.$^5$ .............................................. A61K 33/04
[52] U.S. Cl. ....................................................... 424/702
[58] Field of Search ......................................... 424/702

[56] References Cited

PUBLICATIONS

Bandaru S. Reddy et al., "Effect of Dietary Excess of Inorganic Selenium during Initiation and Post-Initiation Phases of Colon Carcinogenesis in F344 Rats", Cancer Research, 48, pp. 1777–1780, Apr. 1, 1988.

Jaya Nayini et al., "Chemoprevention of Experimental Mammary Carcinogenesis by the Synthetic Organoselenium Compound, Benzylselenocyanate, in Rats", Carcinogenesis, vol. 10, No. 3, pp. 509–512, 1989.

Shigeyuki Sugie et al., "Inhibition by Dietary Benzylselenocyanate of Hepatocarcinogenesis Induced by Azoxymethane in Fischer 344 Rats", Jpn. J. Cancer Res., 80, pp. 952–957, Oct. 1989.

Bandaru S. Reddy et al., "Inhibitory Effect of Dietary p-Methoxybenzeneselenol on Azoxymethane-Induced Colon and Kidney Carcinogenesis in Female F344 Rats", J. Natl. Cancer Inst., vol. 74, No. 6, pp. 1325–1328, Jun. 1985.

Bandaru S. Reddy et al., "Chemoprevention of Colon Carcinogenesis by Dietary Organoselenium, Benzylselenocyanate, in F344 Rats", Cancer Research, 47, pp. 5901–5904, Nov. 15, 1987.

*Primary Examiner*—John W. Rollins
*Attorney, Agent, or Firm*—Ladas & Parry

[57] ABSTRACT

It is shown that benzylselenocyanate in the diet significantly inhibits the incidence (percentage of animals with tumors) and multiplicity (number of tumors per animal) of adenocarcinomas in the colon and multiplicity of adenocarcinomas in the small intestine compared to those fed a control diet. Selenium-dependant glutathione peroxidase activity is significantly increased in kidneys and colon and small intestinal mucosae of animals fed a benzylselenocyanate diet compared to animals fed control diets. BSC in the diet is a superior inhibitor to both its sulfur analog BTC and the inorganic selenium (sodium selenite) during the initiation phase of carcinogenesis.

4 Claims, No Drawings

METHOD AND COMPOSITION FOR INHIBITING COLON CARCINOGENESIS

FIELD OF THE INVENTION

This invention relates to chemoprevention of colon carcinogenesis by dietary compositions and to related methods.

BACKGROUND OF THE INVENTION

A large body of evidence in animal models indicates that supplementation of the diet or drinking water with inorganic selenium in the form of sodium selenite protects against cancer induced by a variety of chemical carcinogens, including cancer of the colon, mammary gland, pancreas, to cite a few. These data have resulted in considerable interest in the potential of selenium as a chemopreventive agent.

Although inorganic selenium has been shown to inhibit carcinogenesis, there is a concern about its toxicity. On a molar basis, selenium salts are the most toxic among the essential elements. Generally, chronic feeding of 5 to 10 ppm of selenium is toxic in animals. Toxic reproductive and teratogenic effects of selenium have been reported for both animals and humans.

Since selenium occurs predominantly as an organic form (selenomethionine) in cereals, vegetables, and grains, attention has been focused to study the effect of organic forms of selenium in carcinogenesis. In methylnitrosourea or 7, 12-Dimethylbenz[a]anthracene induced mammary carcinogenesis, dietary inorganic selenium (4 to 6 ppm) provided greater inhibition of mammary carcinogenesis in female rats than did an equivalent amount of selenium in the form of selenomethionine (Thompson, H. J., Meeker, L. D., and Kokosa, S. Effect of an inorganic and organic forms of dietary selenium on the promotional stage of mammary carcinogenesis in the rat. Cancer Res., 44: 2803-2806, 1984.) In addition, 6 ppm selenium in the form of selenomethionine caused liver damage as indicated by extensive necrosis and fibrosis. Ibid. These observations have shown the need to identify and develop novel forms of organoselenium compounds that are less toxic and more effective than inorganic forms and that can be used effectively as chemopreventive agents. While it has been recognized that synthetic organoselenium compounds offer greater promise for the chemoprevention of cancer, in that their chemical structures can be tailored to provide maximal chemopreventive efficacy with minimal toxicity, the identification and development of a novel selenium compound that is less toxic than previously identified compounds and that possesses tumor-inhibitory effect against colon carcinogenesis has not heretofore been made.

Previously, one of the inventors synthesized two organoselenium compounds, p-methoxybenzenenselenol ("MBS") and benzylselenocyanate ("BSC"), which were found to be effective inhibitors of benzo(a)pyrene-induced forestomach tumors in mice (El-Bayoumy, K. Effect of organoselenium compounds on induction of mouse forestomach tumors by benzo(a)pyrene. Cancer Res., 45: 3631-3635, 1985.) Feeding of 50 ppm MBS in a semipurified diet containing high fat 2 wk before, during, and 1 wk after carcinogen treatment inhibited azoxymethane ("AOM")-induced colon, kidney, and hepatocarcinogenesis in rats. (Reddy, B. S., Tanaka, T., and El-Bayoumy, K. Inhibitory effect of dietary p-methoxybenzeneselenol on azoxymethane-induced colon and kidney carcinogenesis in female F344 rats. J. Natl. Cancer Inst., 74: 1325-1328, 1985; Tanaka, T., Reddy, B. S., and El-Bayoumy, K. Inhibition by dietary organoselenium p-methoxybenzeneselenol, of hepatocarcinogenesis induced by azoxymethane in rats. Jpn. J. Cancer Res. (Gann), 76: 462-467, 1985). It has now been found that BSC in the diet significantly inhibits the incidence and multiplicity of adenocarcinomas in the colon and multiplicity of adenocarcinomas in the small intestine.

SUMMARY OF THE INVENTION

It is an object of the invention to inhibit colon carcinogenesis using dietary means.

It is another object of the invention to develop an organoselenium compound that is less toxic and more effective than inorganic forms and that can be used effectively as a chemopreventive agent.

It is yet another object of the invention to increase the levels of glutathione peroxidase activity in colon and small intestinal mucosae to increase the enzyme-dependent detoxifying system in these tissues.

It is a further object of the invention to develop a new use for benzylselenocyanate as a chemopreventive agent to inhibit colon carcinogenesis.

In accordance with the above and other objects of the invention, there is provided a process of inhibiting azoxymethane-induced colon carcinogenesis in the initiation or postinitiation phase comprising feeding a patient to be treated with a dietary composition comprising an organoselenium compound which is benzylselenocyanate. The dietary composition may comprise benzylselenocyanate in an amount of, for example, 25 ppm.

There is also provided, in accordance with the invention, a process for increasing the enzyme-dependent detoxifying system in the colon and small intestinal mucosae of a patient to be treated by increasing levels of glutathione peroxidase activity in these tissues. This may be done by administering to the patient a diet containing benzylselenocyanate.

There is further provided in accordance with the invention, a dietary composition useful in inhibiting colon carcinogenesis comprising benzylselenocyanate. The composition may comprise benzylselenocyanate in an amount of about 25 ppm. It may also comprise, by way of example, casein in an amount of about 20%; DL-methionine in an amount of about 0.3%; corn starch in an amount of about 52%; dextrose in an amount of about 13%; corn oil in an amount of about 5%; cellulose (e.g. Alphacel) in an amount of about 5%; one or more minerals in an amount of about 3.5%; one or more vitamins in an amount of about 1%, and choline bitartrate in an amount of about 0.2%.

The above objects, features and advantages of the invention will be supplemented by those to be found in the Detailed Description which follows hereinbelow.

DETAILED DESCRIPTION

It has now been found that the synthetic organoselenium compound, BSC, inhibits AOM-induced tumors in the colon and, to a certain extent, in the small intestine. BSC also inhibits AOM-induced metastasis in several organs.

It has also been demonstrated that the feeding of a BSC diet causes an increase in selenium-dependent glutathione peroxidase activity in the kidney, colon, and small intestine, whereas it has no effect on this enzyme activity in the liver and plasma.

Benzylselenocyanate may be prepared from benzylbromide (Aldrich Chemical Co., Milwaukee, Wis.), and potassium selenocyanate (Thiokol/Ventron) as described in Fredga, A., Gronowitz, S., and Hornfeldt, A-B. $^{77}$Se NMR studies of organoselenium compounds, Chem. Scr. 8: 15-19, 1975, or with slight modification. As described in Fredga et al., the compounds may be prepared in the conventional way from the corresponding benzyl chlorides or bromides and potassium selenocyanate in ethanolic or methanolic solution at room temperature. Reaction with heating gives a product somewhat contaminated by diselenide, which is difficult to remove. The reaction mixture may be left to stand for 3-5 days (chlorides react more slowly than bromides). The potassium halide is filtered off and washed with the solvent. The combined filtrates are then evaporated to dryness with a fan or a strong current of air; due to the obnoxious smell an effective hood is desirable. An alternative way to isolate the product is to add excess water, which dissolves the potassium halide and precipitates the organic selenocyanate. The product is recrystallized from dilute ethanol or methanol. Prolonged heating should be avoided. The pure compounds are colourless and crystallize very readily.

In a preferred modification, instead of using methanol or ethanol for the synthesis of BSC—which, in that event, takes a few days—acetone may be used as the solvent and the reaction takes place in 3-4 hours with an improved yield.

The product may be sublimed at 68°-75° C. (2.5 Torr) using a dry ice acetone condensor to give pale yellow needles in 93% yield (m.p. 70.5°-71° C.; literature 70°-71° C. It has a characteristic odor like burnt rubber. IR (CHCl$_3$) gives an absorption at 2140 to 2150 cm$^{-1}$, characteristic of C≡N stretching vibration; nuclear magnetic resonance (CDCl$_3$): δ4.31 (s, 2H), 7.35 (s, 5H); MS (m/e, relative intensity) 197 (M+, 93), 195 (M+, 50), 106(M+-benzyl, 100).

A diet comprising benzylselenocyanate may be prepared and an assay for stability of the benzylselenocyanate may be, made, for example, in accordance with the discussion which follows.

A semipurified diet to which benzylselenocyanate may be added may be prepared as detailed in American Institute of Nutrition. Second report of the Ad Hoc Committee on Standards for Nutritional Studies. J.Nutr., 110: 1726, 1980; and Reddy, B. S., and Maeura, Y. Tumor promotion by dietary fact in azoxymethane-induced colon carcinogenesis in female F344 rats: influence of amount and source of dietary fat. J. Natl. Cancer Inst., 72: 745-750, 1984.

The composition of this semipurified diet is as follows: casein, 20%; DL-methionine, 0.3% corn starch, 52.0%; dextrose, 13.0%; corn oil, 5%; mineral mix (AIN-76), 3.5%; vitamin mix (AIN-76A), 1%; and choline bitartrate, 0.2%. BSC may be added to the semipurified diet at a level of 25 ppm. The AIN-76A (control) diet contains 0.1 ppm selenium in its inorganic form (sodium selenite). An experimental BSC diet may contain, in addition to 0.1 ppm inorganic selenium, 10 ppm selenium. The incorporation of BSC into the semipurified diet may be done with a V-blender after BSC is premixed with a small quantity of diet in a food mixer to ensure uniform distribution of this compound. The stability of BSC in the diet during 10 min, 24 h, and 48 h at room temperature and during 2 wk at 4° C. may be confirmed by high-pressure liquid chromatography analysis. Control and experimental diets may be prepared twice weekly for use in experimental procedures of the type conducted by the inventors, and discussed hereinbelow, which show the efficacy of employing benzylselenocyanate to inhibit colon carcinogenesis.

Experimental Procedure. Male F344 rats received at weaning were quarantined for 10 days and given access to AIN-76A semipurified diet (control diet). They were then be randomly allocated by weight to one of three dietary groups (control diet and 25 ppm BSC and 25 ppm benzylthiocyanate ("BTC") diets). BTC has been used previously in the literature as an inhibitor of carcinogenesis induced by chemicals in experimental animals. Therefore one of our goals was to compare BSC with its sulfur analog BTC. Each dietary group was divided into AOM-treated (27 animals per subgroup) and vehicle-treated (12 animals per subgroup) subgroups and housed in plastic cages with filter tops in the animal holding room under controlled environmental conditions.

Beginning at 5 wk of age, groups of rats fed the control diet were transferred to diets containing 25 ppm BSC or 25 ppm BTC. At 7 wk of age, the animals in each group, except the vehicle-treated controls, received two weekly s.c. injections of AOM at a dose level of 15 mg/kg body weight/wk. Vehicle controls were treated with an equal volume of normal saline. One wk after AOM or saline treatment, animals receiving the BSC and BTC diets were transferred to the control diets and continued on this diet until the termination of the experiment. The 1-wk delay before transferring to control diet was to ensure complete metabolism and excretion of the carcinogen. The animals receiving the control diet continued on the same diet. The experiment was terminated 34 wk after the last AOM injection.

Body weights were recorded weekly until the animals reach 16 wk of age and then every 4 wk. Six vehicle-treated animals randomly chosen from each dietary group while they were consuming experimental and control diets were used for tissue and blood plasma glutathione peroxidase analysis.

Both AOM-and vehicle-treated animals were sacrificed by CO$_2$ euthanasia. Following laparotomy, the entire stomach, small intestine, and large intestine were resected and opened longitudinally, and the contents flushed with normal saline. The location, number, and size of the colon and small intestinal tumors were noted grossly under the dissection microscope. All other organs, including liver and kidneys, were also examined grossly for tumors. Tissues were fixed in 10% buffered formalin, embedded in paraffin blocks, and processed by routine histological methods with the use of eosin and hematoxylin stains.

Biochemical Determination. For the determination of tissue and blood plasma glutathione peroxidase activity, 6 vehicle-treated animals from each dietary group, while the animals were on experimental and control diets, were used. Before sacrificing the animals, blood was obtained under ether anesthesia by cardiac puncture with a syringe. They were then decapitated, and liver, kidneys, small intestine, and colon were rapidly removed. The liver was perfused with ice-cold normal saline. The small intestine and colon were slit open longitudinally and freed from all the contents, and the mucosa was scraped with a microscope glass slide. The liver and kidneys were trimmed free of connective tissue, minced with scissors, and homogenized for 10 s in 3 volumes of buffer, pH 7.3 (0.25 sucrose-10 mM EDTA-50 mM potassium phosphate) using a Brinkman Polytron at low speed. The colonic and small intestinal mucosal scrapings were immediately placed into 3 volumes of the same buffer and homogenized similarly. The homogenates were centrifuged in a Sorvall RC-2B centrifuge at 10,000×g, 4° C., for 20 min. The supernatant was centrifuged in a Beckman Ultracentrifuge at 100,000×g, 4° C., for 1 h. The resulting cytosol fraction was used for determination of glutathione peroxidase activity and protein.

Glutathione peroxidase activity was determined spectrophotometrically according to a modification of the enzyme-coupled assay procedure of Paglia and Valentine. The reaction mixture consisted of 50 mM potassium phosphate buffer (pH 7.0), 1 mM EDTA, 0.2 mM NADPH, 1 enzyme unit/ml oxidized glutathione-reductase, 1 mM glutathione, and 1.5 mM cumene hydroperoxide in a total volume of 1 ml. The cytosol was added to the above mixture and allowed to incubate 5 min. at room temperature. Total glutathione peroxide was measured with cumene hydroperoxide as a substrate. Selenium-dependent glutathione peroxide was measured with tert-butyl hydroperoxide. The reaction was started with the addition of substrate solution. Absorbance was measured at 340 nm, and activity was measured from the slope of the lines as mol NADPH oxidized/min/mg protein. Blank reactions without cytosol were run simultaneously. Protein concentration in the cytosol fraction was measured by the method of Lowry et al. with bovine serum albumin as standard.

Statistical Analysis. The data on tumor incidence were analyzed statistically by the $x^2$ method and Fischer's exact probability test, and tumor multiplicity was analyzed by Student's t test. Biochemical results were analyzed by Student's t test.

EXPERIMENTAL RESULTS

Using the above-identified procedures, a study was made of the effect of feeding benzylselenocyanate and its sulfur analogue, benzylthiocyanate, two (2) weeks before, during and until one (1) week after carcinogen administration (initiation phase) on intestinal carcinogenesis induced by azoxymethane (CAS: 25843-45-2) in male F344 rats.

General Observations. There was no evidence of toxicity in the animals fed BSC and BTC diets. Body weights of animals fed the experimental and control diets and treated with AOM or vehicle were comparable (Table 1). However, as expected, the body weights of AOM-treated animals in all dietary groups were slightly lower than the vehicle-treated animals during the terminal part of the study because of tumor burden and consequent reduction in body weight.

Tumor Incidences. Table 2 summarizes AOM-induced colon tumor incidences (percentage of animals with tumors) and colon tumor multiplicity (number of tumors/animal). One animal from the BTC group died 2 wk after AOM treatment and was not included in the results. The incidences of AOM-induced total colon tumors as well as adenocarcinomas of the colon were significantly lower in rats fed the BSC diet than in those fed the control diet. There were no differences in colon tumor incidences between the animals fed the control diet and BTC diet. With regard to colon tumor multiplicity, the number of total colon tumors (adenomas and adenocarcinomas) and the number of adenocarcinomas per animal were significally inhibited in animals fed the BSC diet compared to those fed the control diet and BTC diet. Although there was a slight inhibition of multiplicity of adenomas in the BSC diet as compared to the control diet and BTC diet, the differences, however, did not reach statistical signficance.

Table 3 shows the incidence and multiplicity of small intestinal tumors and incidence of ear duct tumors. Although the differences in the incidence of small intestinal tumors among the dietary groups were not significant, feeding of the BSC diet slightly reduced the incidence of small intestinal adenocarcinomas. Small intestinal tumor multiplicity was significantly inhibited in animals fed the BSC diet compared to those fed the BTC diet and control diet. A significant inhibition in the multiplicity of small intestinal adenocarcinomas was observed in animals fed the BSC diet compared to those fed the control diet. There was a slight but not significant difference in ear duct tumor incidences among the dietary groups. Two animals in the BSC diet group, 8 animals in the control diet group, and 5 animals in the BTC diet group developed ear duct tumors. Two animals in the control diet groups developed metastases in several organs, whereas none of the animals in BSC and BTC diet groups developed metastasis.

Biochemical Observations. Table 4 summarizes the selenium-dependent glutathione peroxidase activity in various tissues. Since there are no differences in the activity of non-selenium-dependent glutathione peroxidase activity among the dietary groups and for simplification of the data, only the values of selenium-dependent glutathione peroxidase activity have been reported in the present study. Selenium-dependent glutathione peroxidase activity of plasma and liver was not affected by various dietary treatments. There was, however, a significant increase in the enzyme activity in kidney and colonic and small intestinal mucosae of animals fed the BSC diet compared to that in those animals fed the BTC diet and control diet.

The effectiveness of BSC in inhibiting colon carcinogenesis, as detailed above, far exceeded any possible expectation. Moreover, although, as shown by a recent study, the inorganic selenium compound, sodium selenite, not only is more toxic than BSC but also does not inhibit colon carcinogenesis during the initiation phase (Reddy, Bandaru S., Sugie, S., Maruyama, H. and Marra, P. Effect of dietary excess of inorganic selenium during initiation and postinitiation phases of colon carcinogenesis in F344 rats. Cancer Res., 48: 1777–1780, 1988), the organoselenium compound BSC inhibited colon tumors during the initiation phase of carcinogenesis. In other words, BSC may be used in inhibiting colon carcinogenesis both during the initiation phase of colon carcinogenesis and the postinitiation phase, after development of colon polyps.

The instant invention may open new approaches to the development of effective and less toxic novel selenium-containing chemopreventive agents. For example, although is too early to determine definitively the optimum dose which will be suitable for human use, we can estimate a dose based on the $LD_{50}$ of BSC in rats (lethal dose at which 50% of the rats die). In a separate study, we have determined the $LD_{50}$ of BSC in rats (125mg/kg body weight). Considering the average human body weight to be 70 kg, the $LD_{50}$ in rats times human body weight to the power 0.75 should yield the approximate $LD_{50}$ in humans, i.e. $125 \times 70^{0.75} = 125 \times 24.2 = 3025$ mg/kg body weight. The extrapolation from rats to humans suggests the approximate $LD_{50}$. An order of magnitude of ten (10) times less than the $LD_{50}$ may be appropriate for humans.

There is also a possibility that the chemopreventive efficacy of these organoselenium compounds can be increased and optimized by systematically altering their molecular structures. Although the present invention has fully been described in connection with a preferred embodiment thereof, it is to be noted that various changes and modifications may be apparent to those skilled in the art. Such changes and modifications are to be understood as included within the true scope of the present invention as defined by the following claims.

TABLE 1

ORGANOSELENIUM INHIBITION OF COLON CANCER
Body weights of male F344 rats fed the experimental diets

| Diet group | No. of rats at start of experiment | Body wt (g) on experimental or control diet at the following wk | | | | | | |
|---|---|---|---|---|---|---|---|---|
| | | Initial wk (Wk 0) | 4 | 8 | 16 | 22 | 30 | 37 (at termination) |
| AOM treated | | | | | | | | |
| Control diet | 27 | 42 ± 3[a] | 178 ± 10 | 285 ± 14 | 350 ± 19 | 388 ± 20 | 435 ± 21 | 454 ± 24 |
| BSC diet | 27 | 40 ± 4 | 174 ± 9 | 279 ± 15 | 348 ± 16 | 390 ± 21 | 430 ± 20 | 449 ± 22 |
| BTC diet | 27 | 40 ± 3 | 180 ± 10 | 281 ± 18 | 356 ± 21 | 394 ± 22 | 432 ± 24 | 459 ± 19 |
| Vehicle treated | | | | | | | | |
| Control diet | 12 | 39 ± 3 | 184 ± 11 | 289 ± 16 | 361 ± 20 | 398 ± 21 | 442 ± 28 | 469 ± 20 |
| BSC diet | 12 | 41 ± 4 | 179 ± 12 | 284 ± 19 | 364 ± 19 | 402 ± 20 | 448 ± 26 | 467 ± 21 |
| BTC diet | 12 | 40 ± 3 | 182 ± 10 | 286 ± 18 | 362 ± 21 | 406 ± 22 | 449 ± 24 | 470 ± 24 |

[a]Mean ± SD.

TABLE 2

Effect of dietary benzylselenocyanate and benzylthiocyanate on azoxymethane-induced colon tumors in male F344 rats
Values in the same column that do not share a common superscript number are significantly different at $P < 0.05$ ($x^2$, Fisher's exact probability test, or Student's t test).

| Dietary group[a] | No. of animal/group | Colon tumor incidence (% of animals with tumors) | | | Colon tumor multiplicity (no. of tumors/animals) | | |
|---|---|---|---|---|---|---|---|
| | | Total[b,c] | Adenoma | Adenocarcinoma | Total[b,d] | Adenoma | Adenocarcinoma |
| Control diet | 27 | 78(21)[1] | 59(16)[1] | 38(10)[1] | 1.62 ± 1.2[e1] (44) | 1.18 ± 1.2[1] (32) | 0.44 ± 0.6[1] (12) |
| BSC diet | 27 | 48(13)[2] | 44(12)[1] | 11(3)[2] | 0.81 ± 1.0[2] (22) | 0.70 ± 0.9[1] (19) | 0.11 ± 0.3[2] (3) |
| BTC diet | 26 | 69(18)[1,2] | 62(16)[1] | 31(8)[1] | 1.62 ± 1.3[1] (42) | 1.27 ± 1.3[1] (33) | 0.35 ± 0.4[1] (9) |

[a]Animals were fed the control diet and BSC and BTC diets 2 wk before, during, and until 1 wk after carcinogen treatment, and then the animals on BSC and BTC diets were transferred to control diet.
[b]Total represents adenomas plus adenocarcinomas.
[c]Numbers in parentheses, number of animals with colon tumors.
[d]Numbers in parentheses, number of tumors per group.
[e]Mean ± SD.

TABLE 3

Effect of dietary benzylselenocyanate and benzylthiocyanate on azoxymethane-induced tumors in male F344 rats
Values in the same column that do not share a common superscript number are significally different at $P < 0.05$ ($x^2$, Fischer's exact probability test, or Student's t test).

| Dietary group[a] | Small intestinal tumor incidence (% of animals with tumors) | | | Small intestinal tumor multiplicity (no. of tumors/animal) | | | % of animals with ear duct tumors | No. of animals with metastasis |
|---|---|---|---|---|---|---|---|---|
| | Total | Adenoma | Adenocarcinoma | Total | Adenoma | Adenocarcinoma | | |
| Control diet | 33(9)[b] | 11(3) | 26(7) | 0.52 0.5[c1] | 0.15 0.4[1] | 0.41 0.7[1] | 29(8) | 2[d] |
| BSC diet | 19(5) | 4(1) | 15(4) | 0.19 0.3[2] | 0.04 0.2[1] | 0.15 0.3[2] | 7(2) | 0 |
| BTC diet | 38(10) | 12(3) | 38(10) | 0.46 0.6[1] | 0.12 0.3[1] | 0.34 0.6[12] | 19(5) | 0 |

[a]Twenty-seven animals were used in the control diet and BSC diet groups and 26 animals in the BTC diet group.
[b]Numbers in parentheses, number of animals with tumors.
[c]Mean ± SD.
[d]One animal had metastasis in liver, pancreas, sleen, and lung, and the other animal had metastasis in liver, pancreas, spleen, prostate, and small intestine.

TABLE 4

Effect of dietary benzylselenocyanate and benzylthiocyanate on selenium-dependent glutathione glutathione peroxidase activity in various tissues of male F344 rats
Values in the same column that do not share a common superscript number are significantly different at $P < 0.05$.

| Dietary group[a] | μmol NADPH oxidized/min/mg protein | | | | |
|---|---|---|---|---|---|
| | Plasma | Liver | Kidney | Colon | Small intestine |
| Control diet | 0.64 0.20[b1] | 1.99 0.40[1] | 0.74 0.24[1] | 0.19 0.04[1] | 0.26 0.02[1] |
| BSC diet | 0.78 0.14[1] | 1.88 0.60[1] | 1.70 0.29[2] | 0.56 0.14[2] | 0.71 0.13[2] |

TABLE 4-continued

Effect of dietary benzylselenocyanate and benzylthiocyanate
on selenium-dependent glutathione glutathione peroxidase
activity in various tissues of male F344 rats
Values in the same column that do not share a common superscript
number are significally different at P <0.05.

| Dietary group[a] | μmol NADPH oxidized/min/mg protein | | | | |
|---|---|---|---|---|---|
|  | Plasma | Liver | Kidney | Colon | Small intestine |
| BTC diet | 0.69 0.16[1] | 1.90 0.66[1] | 0.64 0.30[1] | 0.23 0.06[1] | 0.20 0.10[1] |

Weanling animals were raised on AIN-76A semipurified (control) diet. Starting at 5 wk of age, animals were transferred to diets containing BSC or BTC and fed for an additional 5 wk.
[b]Mean ± SE (n = 6).

What is claimed is:

1. A method for inhibiting azoxymethane-induced colon tumorigenesis in a mammal comprising feeding said mammal a dietary composition comprising an organoselenium compound which is benzylselenocyanate in an amount effective to inhibit said tumorigenesis.

2. A method as claimed in claim 1 wherein the benzylselenocyanate is present in the dietary composition at a level of 25 ppm.

3. A method for increasing the levels of glutathione peroxidase activity in the colon of a mammal comprising feeding the mammal benzylselenocyanate.

4. A dietary composition comprising benzylselenocyanate admixed with a foodstuff, wherein the benzylselenocyanate is present in an amount of about 25 ppm, said dietary composition further comprising casein in an amount of about 20%; DL-methionine in an amount of about 0.3%; corn starch in an amount of about 52%; dextrose in an amount of about 13%; corn oil in an amount of about 5%; cellulose in an amount of about 5%; one or more minerals in an amount of about 3.5%; one or more vitamins in an amount of about 1%; and choline bitartrate in an amount of about 0.2%.

* * * * *